United States Patent [19]

Oe et al.

[11] Patent Number: 4,808,593
[45] Date of Patent: Feb. 28, 1989

[54] BENZOPYRANOPYRIDINEACETIC ACID ESTER COMPOUNDS AND THEIR PHARMACEUTICAL USES

[75] Inventors: Takanori Oe, Oita; Kazuyuki Kawasaki, Fukuoka; Michio Terasawa; Tomonori Imayoshi, both of Oita, all of Japan

[73] Assignee: Yoshitomi Pharmaceutical Industries, Ltd., Osaka, Japan

[21] Appl. No.: 173,909

[22] Filed: Mar. 28, 1988

[30] Foreign Application Priority Data

Mar. 27, 1987 [JP] Japan .................. 62-73485

[51] Int. Cl.$^4$ .................. C07D 491/052; A61K 31/44
[52] U.S. Cl. ...................... 514/291; 546/089
[58] Field of Search ............ 514/291; 546/89

[56] References Cited

U.S. PATENT DOCUMENTS 3,931,205  1/1976  Nakanishi et al. .................. 546/89
4,716,167  12/1987  Nohara et al. ...................... 514/291

Primary Examiner—Alan L. Rotman
Attorney, Agent, or Firm—Sughrue, Mion, Zinn, Macpeak & Seas

[57] ABSTRACT

Benzopyranopyridineacetic acid ester compounds of the formula:

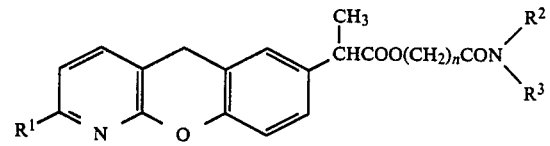

wherein $R^1$, and $R^2$ and $R^3$ independently represent hydrogen or $C_{1-4}$ alkyl; and n is 1 or 2, and their pharmaceutical use are disclosed.

These compounds possess antiinflammatory, analgesic and antipyretic activities with less adverse action on the gastrointestinal tract.

4 Claims, No Drawings

BENZOPYRANOPYRIDINEACETIC ACID ESTER COMPOUNDS AND THEIR PHARMACEUTICAL USES

BACKGROUND OF THE INVENTION

The present invention relates to a new benzopyranopyridineacetic acid ester compound possessing antiinflammatory, analgesic and antipyretic activities.

Benzopyranopyridineacetic acid compounds having analgesic and antiinflammatory effects are disclosed in U.S. Pat. No. 3931205, and their isopropyl and dimethylaminoethyl ester compounds etc. are disclosed in Japanese Published Examined Patent Application Nos. 28639/1976 and 61759/1977.

Having excellent effects, acidic nonsteroidal anti-inflammatory drugs are now widely used, but it is necessary to pay much attention to their clinical application because they are strong in adverse action on the gastrointestinal tract. For this reason, drugs which are weak in such adverse action are desired.

Benzopyranopyridineacetic acids exhibit excellent pharmacological actions such as antiinflammatory, analgesic and antipyretic actions, but considerable adverse action on the gastrointestinal tract is also noted. It is also recognized that the above-mentioned isopropyl and dimethylaminoethyl ester compounds are noticeably weaker in pharmacological activities than their precursor acetic acid compounds.

Taking note of this fact, the present inventors made intensive investigations with the aim of weakening adverse actions such as gastrointestinal disorder without spoiling the excellent pharmacological activities of benzopyranopyridineacetic acid compounds. As a result, the present inventors found that a new benzopyranopyridineacetic acid ester compound is noticeably less severe in adverse action on the gastrointestinal tract than its precursor acetic acid compounds, but also possesses pharmacological activities, in relation to antiinflammatory, analgesic and antipyretic actions, which are nearly equivalent to those of its precursors or more, and completed the present invention.

SUMMARY OF THE INVENTION

Accordingly, it is the object of the present invention to provide a novel benzopyranopyridineacetic acid ester compound possessing antiinflammatory, analgesic and antipyretic activities, and characteristically weak adverse action on the gastrointestinal tract.

Another object of the present invention is to provide a pharmaceutical composition containing the novel benzopyranopyridineacetic acid ester compound as the active ingredient for the improvement or treatment of inflammation, pain, fever, arthritis or rheumatism.

Further object of the present invention is to provide a method of improving or treating inflammation, pain, fever, arthritis or rheumatism by administering the benzopyranopyridineacetic acid ester compound to the subject in need of improvement or treatment.

DETAILED DESCRIPTION

Accordingly, the present invention relates to a benzopyranopyridineacetic acid ester compound represented by the general formula:

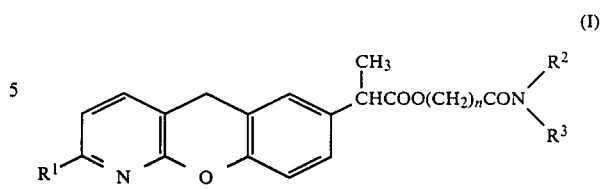

wherein $R_1$, $R_2$ and $R_3$ independently represent hydrogen or alkyl having 1 to 4 carbon atoms; and n represents the integer 1 or 2.

In the above definitions and present specification, an alkyl having 1 to 4 carbon atoms means methyl, ethyl, propyl, isopropyl, butyl, isobutyl, secondary butyl and tertiary butyl.

Preferable compounds of the formula (I) include N,N-dimethylcarbamoylmethyl α,2-dimethyl-5H-[1]benzopyrano[2,3-b]pyridine-7-acetate, carbamoylmethyl α-methyl-5H-[1]benzopyrano [2,3-b]pyridine-7-acetate, carbamoylmethyl α,2-dimethyl5H- [1]benzopyrano[2,3-b]pyridine-7-acetate, 2-carbamoylethyl α,2-dimethyl-5H-[1]benzopyrano[2,3-b]pyridine-7-acetate, N,N-diethylcarbamoylmethyl α,2-dimethyl-5H-[1]benzopyrano[2,3-b]pyridine-7-acetate and N-methylcarbamoylmethyl α,2-dimethyl5H- [1]benzopyrano[2,3-b]pyridine-7-acetate.

The present invention also relates to a pharmaceutical composition for the improvement or treatment of inflammation, pain, fever, arthritis or rheumatism which comprises, a therapeutically effective amount of the compound of formula (I) and a pharmaceutically acceptable additive therefor.

Further, the present invention relates to a method of improving or treating inflammation, pain, fever, arthritis or rheumatism comprising administering to a subject in need of improvement or treatment on a therapeutically effective amount of the compound of formula (I).

The compound of the general formula (I) of the present invention can be produced by the methods (a) through (c) described below, but these methods are no more than examples, and the compound can also be produced by other usual methods which can be employed in the organic chemistry field.

(a) The method in which an acetic acid derivative of the general formula:

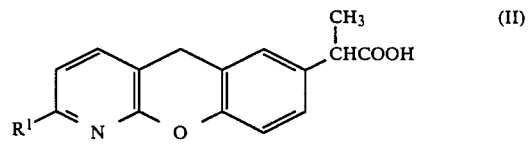

wherein $R_1$ has the same meaning as defined above, is reacted with a compound of the general formula:

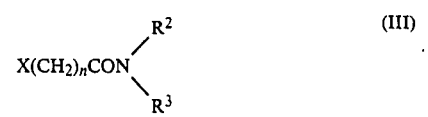

wherein X represents a reactive atom or group (halogen atom such as chlorine, bromine or iodine atom, or an organic sulfonyloxy group such as methanesulfonyloxy, benzenesulfonyloxy or p-toluenesulfonyloxy); the other symbols have the same meanings as defined above, preferably in the presence of a base (e.g., inorganic base such as potassium carbonate, sodium carbonate, sodium hydrogencarbonate, sodium hydroxide or potassium hydroxide; or organic base such as triethylamine, pyridine, N-methylmorpholine or dimethylaniline), at 0° to 100° C. for 1 to 24 hours in an inert solvent such as dimethylformamide, dimethylsulfoxide, chloroform, methylene chloride, dichloroethane, dioxane, toluene, pyridine, ethanol, acetone or a mixture thereof.

(b) The method in which a compound of the general formula (II) is reacted with an alcohol derivative represented by the general formula:

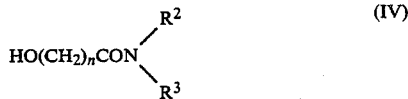

(IV)

wherein the symbols have the same meaning as defined above, in the presense of a dehydrating agent (e.g., sulfuric acid, hydrogen chloride, polyphosphoric acid, p-toluenesulfonic acid) at 50° to 150° C. for 1 to 24 hours in an inert solvent such as toluene, N-methylpyrrolidone, chloroform or mixture thereof.

(c) The method in which a reactive derivative [e.g., acid chloride, acid anhydride, mixed acid anhydride, active ester compound (ester with p-nitrophenol, 1-hydroxybenzotriazole, N-hydroxysuccinimide, etc.)] of a compound of the general formula (II) is reacted with a compound of the general formula (IV), in the presence of a base (e.g., pyridine, triethylamine, potassium carbonate, sodium carbonate, sodium hydroxide, sodium hydrogencarbonate) as required, at −10° to 100° C. for 30 minutes to 24 hours in an inert solvent such as chloroform, methylene chloride, dichloroethane, tetrahydrofuran, dioxane, dimethylformamide, acetonitrile or a mixture thereof.

Optical isomers are present in compounds of the general formula (I) produced by the above methods, and these isomers and mixtures thereof are all involved in the present invention. When desired, optically active isomer can be obtained preferably by converting a compound of the general formula (II) to an optically active isomer by known means such as fractional crystallization and various chromatographies, and carrying out reaction between this optically active isomer and a compound of the general formula (III) or (IV).

The pharmacological actions of the compound of the present invention will now be described by means of some test data. In the action tests, the compound of Example 1 was used as the subject compound, and α,2-dimethyl-5H-[1]benzopyrano[2,3-b]pyridine-7-acetic acid as the reference compound.

1. Action on acute inflammation

A test was carried out in accordance with the method of Winter et al. [Proceedings of the Society for Experimental Biology and Medicine, vol. 111, p. 544 (1962)]. Male Donryu rats weighing about 140 g which had not been fed for 18 hours were used as experimental animals with each experimental group consisting of 5 rats. A solution of the subject compound was orally administered. One hour later, 0.05 ml of a physiological saline solution containing 1% carrageenin was subcutaneously injected via right hind paw pad; 3 hours later, paw volume was measured by the water replacement method (Muromachi Kikai Co., Ltd., MK-500). For effect evaluation, inhibitory rate relative to control group was determined from the rate of increase in paw volume after administration of the phlogogenic substance, and $ED_{50}$ value was calculated by the linear regression method. As a result, the compound of Example 1 showed an $ED_{50}$ value of 0.32 mg/kg, while the reference compound 0.62 mg/kg.

2. Action on chronic inflammation

A test was carried out in accordance with the method of Newbould [British Journal of Pharmacology, vol. 21, p. 127 (1963)]. 10-week-old male Lewis rats were used as experimental animals. To each rat 0.5 mg/0.1 ml of dead tubercle bacillus (R35 H5 type) in suspension in liquid paraffin was intracutaneously inoculated via tail base. On the 15th day, animals presenting arthritis were selected so that each group consisted of 7 animals. A solution of the subject compound was orally administered once a day (5 ml/kg) during the period between the 15th and 24th days. For effect evaluation, inhibitory rate relative to control group was determined from the rate of change in paw volume of the 24th day, calculated on the basis of the paw volume of the 15th day, and the dose indicating the decrease of paw volume than the paw volume of the 15th day was taken as the minimum effective dose (MED, mg/kg). As a result, the compound of Example 1 and the reference compound both exhibited an MED value of 0.3 mg/kg.

3. Analgesic action

A test was carried out in accordance with the method of Koster et al. [Federation Proceedings, vol. 18, p.412 (1959)]. Female ddY mice weighing 18 to 25 g were used as experimental animals with each group consisting of 6 to 18 mice. A solution of the subject compound, at a dose of 10 ml/kg, was orally administered. One hour later, a physiological saline solution containing 1% acetic acid was intraperitoneally administered at a dose of 10 ml/kg. The frequency of stretch symptom found during the 20-minute period following the administration was counted, and inhibitory rate relative to control group was determined, and $ED_{50}$ value was calculated by the linear regression method. As a result, the compound Example 1 of the present invention showed an $ED_{50}$ value of 1.0 mg/kg, while the reference compound, 4.8 mg/kg.

4. Antipyretic action

White rabbits weighing about 3 kg were used as experimental animals with each group consisting of 3 rabbits. Each animal was fixed to a wooden yoke, and its rectal temperature was measured at intervals of 30 minutes. After body temperature became constant, lipopolysaccharide (LPS, Escherichia coli 0-127:B8), as a pyrogen, was injected at a dose of 1 γ/kg via ear vein, whereby each animal was made to have fever. A solution of the subject compound was orally administered (5 ml/kg) 1 hour after the injection of the pyrogen. Using the area below the fever curve for the following 5 hours as a fever index, inhibitory rate relative to control group was determined, and an $ED_{50}$ value was calculated on the graph.

As a result, the compound of Example 1 showed an $ED_{50}$ value of 1.8 mg/kg, which is almost equivalent to the value of the reference compound (1.6 mg/kg).

5. Gastric ulcer inducing action in rat

Male Donryu rats weighing 150 to 200 g were used as experimental animals with each group consisting of 5 rats. A solution of the subject compound, at a dose of 10 ml/kg, was orally administered. 24 hours later, each animal was slaughtered by exsanguination, and the gastric mucomembrane tissue was fixed by injection of 50% ethanol into the stomach. After a specified time elapsed, the stomach was incised along the major curvature, and the tissue was visually examined for the formation of ulcers, whereby ulceration rate was determined, and a $UD_{50}$ value was calculated on the graph. As a result, the compound of Example 1 showed a $UD_{50}$ value of 50 mg/kg, while the reference compound, 20 mg/kg.

The compound of Example 1, at a dose of 100 mg/kg, was orally administered to male Donryu rats, and observations were made for 7 days; no lethal case was noted.

As is obvious from these results of pharmacological tests, it was proven that the compound of the present invention exhibits effects which are equivalent to or even more than those of known compound, and also noticeably reduces ulceration rate in the stomach. This is attributable to the specificity of the ester residue of the compound of the present invention, and is suggestive of usefulness thereof as an excellent antiinflammatory, analgesic and antipyretic drug with less adverse action on the gastrointestinal tract.

The compound of the present invention, when used as a drug for the improvement or treatment of inflammation, pain, fever, arthritis or rheumatism, can be orally or parenterally administered in the form of powder, granules, capsules, tablets, injection, drip infusion, suppository, ointment, eye lotion, etc., singly or in combination with pharmaceutically acceptable and conventional additives such as carrier, excipient, diluent or solubilizer. Thus the pharmaceutical composition contain a therapeutically effective amount of the compound (I) of the present invention, and the pharmaceutically acceptable additive therefor. Dosage varies depending upon type of disease to be treated, symptoms, age, administration method, etc, but it is usual that 10 to 300 mg for each adult is given daily in single or multiple dosages in case of oral administration.

FORMULATION EXAMPLE 1

Capsule containing 25 mg of the active ingredient

| | |
|---|---|
| Compound of Example 1: | 25 mg |
| Lactose: | 37 mg |
| Microcrystalline cellulose: | 18 mg |
| Corn starch: | 7 mg |
| Talc: | 13 mg |
| | 100 mg |

The above substances are capsuled to prepare capsules containing 25 mg of the active ingredient.

FORMULATION EXAMPLE 2

Tablet containing 25 mg of the active ingredient

| | |
|---|---|
| Compound of Example 1: | 25 mg |
| Lactose: | 45 mg |
| Talc: | 4.4 mg |
| Microcrystalline cellulose: | 31.2 mg |
| Corn starch: | 18.5 mg |
| Magnesium stearate: | 0.9 mg |
| | 125 mg |

This tablet, if desired, can be prepared as sugar coated tablets or film coated tablets.

The present invention will now be described in more detail by means of the following examples, but the invention is never limited by any of these examples.

EXAMPLE 1

Under a nitrogen atmosphere, 5.4 g of α,2-dimethyl-5H-[1]-benzopyrano [2,3-b]pyridine-7-acetic acid is dissolved in 22 ml of dimethylformamide, whereafter 1.9 g of potassium carbonate and 2.7 g of N,N-dimethyl-2-chloroacetamide are added, and the mixture is stirred at 75° C. for 2 hours. Under cooling with ice, 50 ml of water is added to the resulting reaction mixture. The precipitated crystals are collected by filtration and washed with water, and then recrystallized from isopropyl alcohol to obtain 6.4 g of N,N-dimethylcarbamoylmethyl α,2-dimethyl-5H-[1]benzopyrano[2,3-b]-pyridine-7acetate as white crystals having a melting point of 150° to 151° C.

EXAMPLE 2

To a suspension of 2.7 g of α,2-dimethyl-5H-[1]benzopyrano[2,3-b]pyridine-7-acetic acid in 20 ml of methylene chloride is added 0.87 ml of thionyl chloride under cooling with ice, and the suspension is stirred until crystals are dissolved, and then concentrated. Under cooling with ice, the residue is added to a solution of 1.1 g of N,N-dimethylglycolic amide in 15 ml of pyridine. After adding the entire amount, the solution is stirred at room temperature for 2 hours. The reaction mixture is poured into ice water. The precipitated crystals are collected by filtration, washed with water, and recrystallized from isopropyl alcohol to obtain 3.3 g of N,N-dimethylcarbamoylmethyl α,2-dimethyl-5H-[1]benzopyrano[2,3-b]pyridine-7-acetate as white crystals having a melting point of 150° to 151° C.

EXAMPLE 3

To a solution of 5.1 g of α-methyl-5H-[1]benzopyrano[2,3-b]pyridine-7-acetic acid in 20 ml of dimethylformamide are added 1.4 g of potassium carbonate and 2.3 g of 2-chloroacetamide, and is stirred at 90° C. for 1 hour under a nitrogen atmosphere. After completion of the reaction, the reaction mixture is poured into ice water. The precipitated crystals are collected by filtration, washed with water, and then recrystallized from ethanol to obtain 6.2 g of carbamoylmethyl α-methyl-5H-[1]benzopyrano[2,3-4-b]pyridine-7-acetate as white crystals having a melting point of 161° to 162° C.

EXAMPLE 4

To a solution of 2.7 g of α,2-dimethyl-5H-[1]benzopyrano [2,3-b]pyridine-7-acetic acid in 15 ml of dimethylformamide are added 0.8 g of potassium carbonate and 1.1 g of 2-chloroacetamide, and stirred at 80° C. for 1 hour under a nitrogen atmosphere. The reaction mixture is poured into ice water, and the precipitated crystals are collected by filtration, washed with water, and then recrystallized from ethanol to obtain 2.7 g of carbamoylmethyl α,2-dimethyl-5H-[1]benzopyrano [2,3-b]pyridine-7-acetate as white crystals having a melting point of 175° to 177° C.

EXAMPLE 5

To a solution of 2.7 g of α,2-dimethyl-5H-[1]benzopyrano [2,3-b]pyridine-7-acetic acid in 15 ml of dimethylformamide are added 0.8 g of potassium carbonate and 1.3 g of 3-chloropropionamide, and stirred at 70° C. for 7.5 hours under a nitrogen atmosphere. The reaction mixture is poured into ice water. The precipitate is extracted with ethyl acetate, washed with water and dried, and then concentrated. The residue is recrystallized from ethanol to obtain 2.4 g of 2-carbamoylethyl α,2-dimethyl-5H-[1]benzopyrano[2,3-b]pyridine7-acetate as white crystals having a melting point of 143° to 145° C.

EXAMPLE 6

To a solution of 2.7 g of α,2-dimethyl-5H-[1]benzopyrano [2,3-b]pyridine-7-acetic acid in 15 ml of dimethylformamide are added 2.1 g of N,N-diethyl-2-bromoacetamide and 1 g of potassium carbonate, and stirred at 40° C. for 1.5 hours under a nitrogen atmosphere. The reaction mixture is poured into ice water. The precipitate is extracted with ethyl acetate, washed with water and dried, and then concentrated. The residue is recrystallized from toluene-hexane to obtain 3.3 g of N,N-diethylcarbamoylmethyl α,2-dimethyl-5H-[]benzopyrano [2,3-b]pyridine-7-acetate as white crystals having a melting point of 72° to 75° C.

EXAMPLE 7

To a solution of 2.7 g of α,2-dimethyl-5H-[1]benzopyrano [2,3-b]pyridine-7-acetic acid in 15 ml of dimethylformamide are added 1 g of potassium carbonate and 1.2 g of N-methyl-2-chloroacetamide, and stirred at 45° C. for 1.5 hours under a nitrogen atmosphere. The reaction mixture is poured into ice water. The precipitated crystals are collected by filtration and washed with water, and then recrystallized from isopropyl alcohol to obtain 3.1 g of N-methylcarbamoylmethyl α,2-dimethyl5H-[1]benzopyrano[2,3-b]pyridine-7-acetate as white crystals having a melting point of 144° to 146° C.

The present invention has been fully explained in the description and examples given above, but any variations and modifications thereof may be made without departing from the spirit and scope of the present invention.

What is claimed is:

1. A benzopyranopyridineacetic acid ester compound of the general formula:

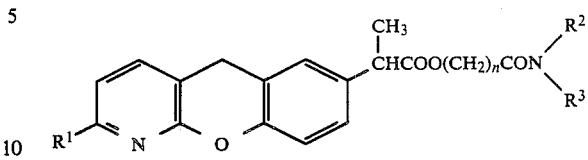

wherein $R_1$, $R_2$ and $R_3$ independently represent hydrogen or $C_{1-4}$ alkyl having 1 to 4 carbon atoms; and n represents the integer 1 or 2.

2. A benzopyranopyridineacetic acid ester compound as claimed in claim 1, wherein said compound is N,N-dimethylcarbamoylmethyl α,2-dimethyl-5H-[1]benzopyrano[2,3-b]pyridine-7-acetate, carbamoylmethyl α-methyl-5H-[1]benzopyrano[2,3-b]pyridine-7acetate, carbamoylmethyl α,2-dimethyl-5H-[1]benzopyrano[2,3-b]pyridine-7-acetate, 2-carbamoylethyl α,2-dimethyl-5H-[1]benzopyrano [2,3-b]pyridine-7-acetate, N,N-diethylcarbamoylmethyl α,2- dimethyl-5H-[1]benzopyrano [2,3-b]pyridine-7-acetate and N-methylcarbamoylmethylα,2-dimethyl-5H-[]benzopyrano[2,3-]pyridine-7-acetate.

3. A pharmaceutical composition for the improvement or treatment of inflammation, pain, fever, arthritis or rheumatism which comprises, a therapeutically effective amount of a benzopyranopyridineacetic acid ester compound as claimed in claim 1 or 2, and a pharmaceutically acceptable additive therefor.

4. A method of improving or treating inflammation, pain, fever, arthritis or rheumatism comprising administering to a subject in need of improvement or treatment on a therapeutically effective amount of a benzopyranopyridineacetic acid ester compound as claimed in claim 1.

* * * * *